United States Patent [19]

Baylink

[11] Patent Number: 5,753,450
[45] Date of Patent: May 19, 1998

[54] BONE RESORPTION ASSAY

[76] Inventor: David J. Baylink, 1428 Serpentine Dr., Redlands, Calif. 92373

[21] Appl. No.: 479,236

[22] Filed: Jun. 7, 1995

Related U.S. Application Data

[63] Continuation of Ser. No. 998,078, Dec. 28, 1992, abandoned.

[51] Int. Cl.$^6$ .................... G01N 33/53; G01N 33/543
[52] U.S. Cl. .................... 435/7.93; 435/7.9; 435/7.92; 435/7.94; 435/70.21; 435/240.27; 435/975; 436/518; 436/540; 436/548; 436/808; 530/387.1; 530/388.1; 530/391.1; 530/391.3; 530/387.9
[58] Field of Search .................... 435/7.9, 7.92, 435/7.93, 7.94, 70.21, 240.27, 975; 436/518, 540, 548, 808; 530/387.1, 388.1, 391.1, 391.3, 387.9

[56] References Cited

U.S. PATENT DOCUMENTS

| | | | |
|---|---|---|---|
| 4,973,666 | 11/1990 | Eyre | 530/323 |
| 5,532,169 | 7/1996 | Eyre | 436/518 |
| 5,538,853 | 7/1996 | Risteli et al. | 435/7.9 |

FOREIGN PATENT DOCUMENTS

| | | |
|---|---|---|
| 0505210 | 9/1992 | European Pat. Off. |
| 2205643 | 12/1988 | United Kingdom |
| 2245568 | 1/1992 | United Kingdom |
| 9221698 | 12/1992 | WIPO |

OTHER PUBLICATIONS

Otter et al., "Type I Collagen α-1 Chain C-Telopeptide: Solution Structure Determined by 600-MHZ Proton NMR Spectroscopy and Implications for its Role in Collagen Fibrillogenesis", *Biochemistry*, vol. 27, pp. 3560-3567 (1988).

Ramirez et al., "Molecular Biology of the Human Fibrillar Collagen Genes", *Ann. N.Y. Acad. Sci.*, vol. 543, pp. 109-116, (1987).

Robins, "An Enzyme-Linked Immunoassay for the Collagen Cross-Link Pyridinoline", *Biochem J.*, 207:617-620 (1982).

Tromp et al., "Structure of a Full-Length cDNA Clone for the Preproα1(I) Chain of Human Type I Procollagen", *Biochem. J.* 253:919-922 (1988).

Zuk et al., "Evaluation of an Immunoassay for Collagen Cross-links", *J. Bone & Min. Res.* 6:(Suppl. 1) 197 (1991).

Eyre et al., "Monitoring Bone Resorption in Early Post-Menopausal Women by an Immunoassay for Cross-Linked Collagen Peptides", *J.Bone & Mineral Res.* 6:(Suppl. 1) 201 (1991).

Hanson et al., "A Specific Immunoassay for Bone Resorption Based on Cross-Linked Collagen Peptides in Urine", *J. Bone & Min. Res.* 6:(Suppl. 1) 669 (1991).

Risteli et al., "Bone Resorption Assay Based on a Peptide Liberated During Type I Collagen Degradation", *J. Bone & Min. Res.* 6:(Suppl. 1) 670 (1991).

Orion Diagnostica, "Telopeptide ICTP [$^{125}$I] Radioimmunoassay Kit", Package Insert (Feb., 1992).

*Primary Examiner*—Susan Wolski
*Attorney, Agent, or Firm*—Popovich & Wiles, P.A.

[57] ABSTRACT

Compositions and methods are provided which are useful in determining the levels of the C-telopeptide of human Type I collagen. The levels of the C-telopeptide are used as a marker of collagen degradation in an individual, and thus serve as a sensitive and specific indicator of bone resorption. Assays for the C-telopeptide find a variety of uses, including use in diagnosing metabolic bone disorders such as osteoporosis or postmenopausal rapid bone losers, monitoring the efficacy of therapeutic regimens designed to treat such disorders, determining the extent of imbalances between bone formation and resorption.

23 Claims, 1 Drawing Sheet

BONE RESORPTION ASSAY

This is a Continuation of application Ser. No. 07/998,078, filed Dec. 28, 1992 now abandoned.

BACKGROUND OF THE INVENTION

This invention relates to a method of measuring bone resorption rates. More specifically, it relates to the use of peptides of the Type I collagen C-telopeptide and antibodies specific to those peptides for the measurement of specific urine and serum peptides produced during the degradation of bone collagen.

Osteoporosis is a widespread disease, afflicting an estimated 15–20 million people in the United States. The disorder is characterized by a decrease in bone mass, which leads to a weakening of the bone. The degree of weakening can be severe enough to result in fractures occurring spontaneously or as a result of minor trauma. Osteoporosis is most common in postmenopausal women with 25% of the women over the age of 60 suffering from spinal compression fractures. Although these fractures are seldom fatal, the continued pain and vertebral deformity are a major source of disability in the elderly. On the other hand, hip fractures not only cause pain and disability, but also lead to death within 6 months of the acute fracture in as many as 15% of patients. That 30% of women have hip fractures by the time they reach age 90 demonstrates the magnitude of this problem. Although most common in postmenopausal women, osteoporosis can also occur in older men and younger amenorrheic women. The annual cost of care for osteoporotic-related injuries is estimated to exceed 7 billion dollars (Barnes, O. M., *Science*, 236:914 (1987)).

Several methods exist for determining bone mass and, thus, diagnosing osteoporosis. Among these are single photon absorptiometry, dual photon absorptiometry, and quantitative computed tomography. Although very good at demonstrating the present density of the bone, these methods are unable to give an accurate determination of the rate of bone loss. Because of this, present methods cannot be used to monitor the efficacy of short-term therapy for the treatment of osteoporosis.

A method of determining the present rate of bone loss would be of great use in monitoring osteoporosis. Assays that are presently used for this purpose are based on the release of a specific amino acid or peptides from degraded collagen, the most common protein found in bone.

Type I collagen is unique to connective tissues and is a major component in bone. Each Type I collagen fiber is composed of three long, helical polypeptide chains (two $\alpha1(I)$ chains and one $\alpha2(I)$ chain) that bind tightly to each other. The normal synthesis and breakdown of this collagen type can be altered during the pathogenesis of many kinds of disease, including osteoporosis. Because bone is a metabolically active tissue throughout life, indicators of Type I collagen turnover could be useful as a markers in metabolic bone disease.

The major means for estimating the metabolic rate of bone collagen has been to quantify the urinary excretion of hydroxyproline, which is derived from collagenous proteins. Unfortunately, this test has proven tedious, associated with several sources of error, and not specific for Type I collagen. Azria, *Calcif. Tissue Int.* 45:7–11 (1989). Hydroxyproline is an amino acid produced as a result of posttranslational modification of proline during collagen synthesis. It is found almost exclusively in collagen. During collagen breakdown, hydroxyproline is released into the serum and cleared from the body in urine. There are, however, some difficulties in using hydroxyproline as a marker of bone resorption. First, hydroxyproline is found in all collagens, not just type I collagen, the type found in bone. Therefore it is not a marker entirely specific for bone. Second, a large portion of the hydroxyproline produced from collagen degradation is metabolized by the liver and never appears in the urine. Finally, it has been suggested that about 10 percent of the urinary hydroxyproline is indicative of bone formation and not resorption, being released during the proteolytic processing of procollagen. Because of these problems, hydroxyproline is not a reliable quantitative method for analysis of bone resorption. Despite these drawbacks, urinary hydroxyproline remains the most commonly used marker for bone resorption.

Hydroxylysine is a second amino acid unique to collagen and collagen-like peptides. Similar to hydroxyproline, hydroxylysine is produced by a posttranslational modification of lysine during collagen synthesis. Unlike hydroxyproline, this amino acid can be further modified by glycosylation to produce galactosyl hydroxylysine (GHyl) and glucosylgalactosyl hydroxylysine (GGHyl). Although hydroxylysine is found in all collagens, the ratio of GHyl to GGHyl is higher in bone tissue than in other collagens, while GGHyl is higher in skin. The urinary GGHyl:GHyl ratio in normal adults is greater than 1.0, whereas in rapidly growing children or in patients with bone disorders, such as Paget's Disease, a disease characterized by increased bone resorption, the ratio of GGHyl to GHyl is less than 1.0. Unlike hydroxyproline, the hydroxylysine glycosides are not significantly metabolized prior to urinary excretion. Because of this, it has been estimated that urinary hydroxylysine glycosides can account for 50–100% of collagen breakdown, as opposed to the 10–25% estimated for hydroxyproline. Although the potential for using urinary hydroxylysine glycoside ratios as markers for bone resorption is great, the existing methods for their determination are tedious, making their measurements impractical outside of a clinical research laboratory. Because of the widespread nature of disease associated with the bone resorption, assays, which cannot be performed by community clinical laboratories, lack general clinical usefulness.

A third group of compounds suggested as potential markers of collagen degradation are pyridinium cross-links. Pyridinium cross-links are derived from the condensation of three hydroxylysine or lysine residues by the action of lysyl oxidase. These compounds have been shown to serve as cross-links between collagen chains and form during the maturation of collagen. Two chemical forms of pyridinium residues have been identified. Hydroxylysyl pyridinoline (HP), also referred to as pyridinoline, is found predominantly in non-bone collagens, such as cartilage. Lysyl pyridinoline (LP), also called deoxypyridinoline, is the form found predominantly in bone and dentin. During collagen breakdown, the pyridinium cross-links are released and cleared by the kidneys. Both compounds are naturally fluorescent with the same excitation and emission spectra. This allows them to be resolved and assayed directly from urine. Unfortunately, the assay involves extensive hydrolysis of urine followed by ion-exchange chromatography and reverse phase high pressure liquid chromatography. Although this method provides reproducible results, it is tedious and does not lend itself to the measurement of large numbers of clinical samples.

An enzyme-linked immunoassay to measure HP urine has been reported (Robins, *Biochem J.*, 207:617–620 (1982)). This assay used a rabbit polyclonal antibody raised against free HP that had been conjugated to bovine serum albumin. Using this assay, Robins was able to demonstrate differences between HP levels in urine from normal adults and patients with arthritic joint diseases. Although Robins was able to demonstrate HP levels in urine at concentrations that were proportional to the rate of joint cartilage resorption, the increase in HP could result from cartilage destruction alone and thus, reliable information on bone resorption could not be obtained from this assay.

Other immunoassays for measuring both HP and LP have been developed. Robins, *Biochem. J.*, 207:617–620 (1982). This assay reacts only with the free crosslinks and does not react with the peptide-bound crosslinks and, thus, is not an accurate reflection of resorption.

Hanson and Eyre, J.Bone & Mineral Res. 6:(Suppl. 1) 251(1991), and Risteli et al., J.Bone & Mineral Res. 6:(Suppl. 1) 251(1991), have reported the development of immunoassays based on cross-linked collagen peptides found either in urine, as described by Eyre, U.S. Pat. No. 4,973,666, or liberated from human femoral bone by enzyme degradation. Both these assays measure levels of pyridinoline crosslinked collagen peptides. Unfortunately, the concentration of the crosslinks in bone is not invariant. The concentration of crosslinks in bone can vary between different types of bone and, furthermore, between the bones of different subjects. The pyridinoline formed in bone is a post-translational modification of the collagen molecule. This post-translational change varies with the nutritional status of the patient, with the hormonal status of the patient, and with the age of the patient, and it varies considerably from patient to patient. The amount of pyridinoline appearing in the serum or urine will be a direct reflection of the amount in bone. Thus, the urine and serum concentrations of both the crosslinks, themselves, and the crosslinked collagen peptides depend not only on the amount of bone resorption, but also on the type of bone being resorbed and the concentration of the crosslinks in the bone. These variables limit the clinical utility of assays which measure pyridinoline or pyridinoline-crosslinked peptides because the amount of bone resorption is not predictably related to the pyridinoline measured.

What is needed is an assay measuring a degradation product of collagen, which is not influenced by diet, hormonal status, age, or disease. The method should be one that can be applied to body fluids, such as serum or urine. The method also should be sensitive and able to determine rapidly bone resorption rates so that it can be used to assess various therapeutic regimens. The present invention fulfills these and other needs.

SUMMARY OF THE INVENTION

Compositions and methods are provided which are useful in determining the levels of the C-telopeptide of human Type I collagen. The levels of the C-telopeptide are used as a marker of Type I collagen degradation in an individual, and, thus, serve as a sensitive and specific indicator of bone resorption. Assays for the C-telopeptide find a variety of uses, including use in diagnosing metabolic bone disorders, such as osteoporosis or postmenopausal rapid bone loss, monitoring the efficacy of therapeutic regimens designed to treat such disorders, determining the extent of imbalances between bone formation and resorption, and bone destruction from Paget's disease or malignancies, etc.

The assays of the present invention employ C-telopeptides of human Type I collagen and antibodies specific to said peptides. More particularly, peptides of the invention comprise from six to fifty amino acids and have at least one epitope, which immunologically competes with the native C-telopeptide of Type I collagen. In a preferred embodiment, the epitope(s) is (are) contained in the sequence Asp-Phe-Ser-Phe-Leu-Pro-Gln-Pro-Pro-Gln-Glu-Lys-Ala-His-Asp-Gly-Gly-Arg (SEQ ID NO:1). The peptides will typically further comprise at least one Cys and/or Tyr residue at the N- or C-terminus to facilitate conjugation, for labeling, and the like. Antibodies, either polyclonal or monoclonal, are provided which bind specifically to a peptide of the invention and thus allow a variety of immunoassay formats. Particularly useful are radioimmunoassays and enzyme-linked immunosorbent assays to conveniently determine levels of C-telopeptide of type I collagen in a sample, such as urine, serum, or plasma, obtained from an individual of interest.

DESCRIPTION OF THE SPECIFIC EMBODIMENTS

Figure 1:
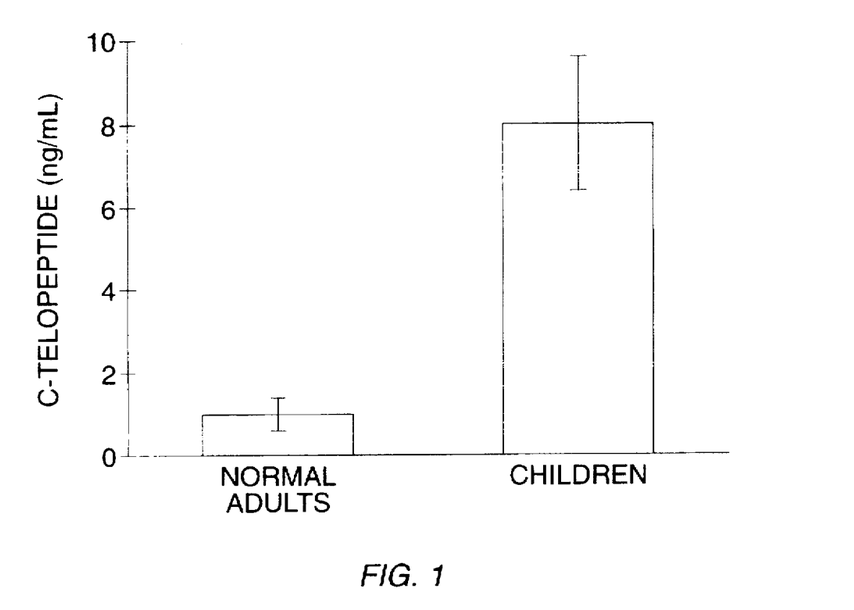
FIG. 1 is a bar graph of C-telopeptide concentration (ng/ml) versus normal adults and children, which illustrates the mean serum concentration of C-telopeptide measured by methods of the present invention in adults and children.
Figure 2:
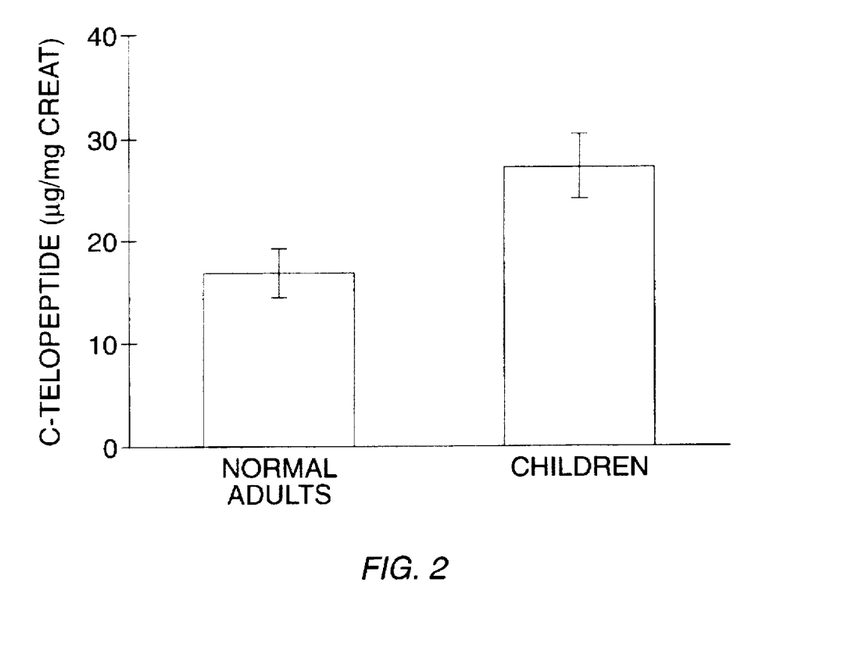
FIG. 2 is a graph of C-telopeptide concentration (μg/ml creatinine) versus normal adults and children, which illustrates the mean urinary C-telopeptide (in micrograms) to creatinine (in milligrams) ratio in normal adults and children.

This invention provides an immunoassay for the C-telopeptide of human Type I collagen, using a synthetic peptide as the antigen. The peptide used is based on a short peptide purified from the urine of a patient with Paget's disease of the bone. One of the characteristics of this disease is increased bone resorption. The peptide excreted into the urine of these patients is an eighteen amino acid peptide produced during the proteolytic breakdown of type I collagen. It consists of amino acids 1036–1053 of the al(I) chain. The synthetic peptide used for this invention consists of the same eighteen amino acids with the addition of a tyrosine and a cysteine at the amino terminal end of the peptide. The purpose of these additions of the two amino acids is to provide a site for binding the peptide to a carrier protein for immunizing animals for antibody production and to provide a site for the radioactive labelling of the peptide. One embodiment of the C-telopeptide of this invention is illustrated in FIG. 1.

The present invention provides a C-telopeptide type I collagen assay to measure a breakdown product of collagen that is independent of the amount of pyridinoline in bone. Moreover, the concentration of this C-telopeptide in collagen is uniform because this C-telopeptide is present in type I collagen molecules. Thus, this assay eliminates the major deficiency of the pyridinoline or pyridinoline peptide assays, which is the variability of pyridinoline content in bone between different patients.

The present invention provides C-telopeptides derived from the procollagen alpha (α)1 chain of Type I collagen for use in compositions and methods for the diagnosis, screening and monitoring of bone formation in an individual. The peptides and/or antibodies thereto are useful in assays to determine the level of type I collagen degradation, and, therefore, provide a specific and sensitive determination of bone resorption.

In some embodiments, the peptides of the present invention are derived from the C-telopeptide region of the α1(I)

chain of Type I collagen. The C-telopeptide extends from residues 1036 to 1053 of the α1(I) chain of Type I collagen, where the numbering is according to Tromp et al., *Biochem. J.* 254:919-922 (1988), which is incorporated herein by reference. Thus, in accordance with the present invention, peptides are provided which contain from six to fifty amino acids and which contain at least one epitope that is immunologically competitive with the native C-telopeptide. Antibodies produced to the peptides, can be used to readily identify those peptides which contain at least one epitope that is immunologically competitive with the native C-telopeptide using well known assay methods. Competition will typically be due to specific binding by the antibody to the peptide epitopes but, in some cases, steric hindrance in epitope conformation may also contribute to the competition. Competition-type assays typically do not determine the actual mechanism of competition.

By "C-telopeptide of the α1(I) chain of Type I collagen" (hereinafter also referred to as "C-telopeptide"), it is meant a contiguous chain containing at least six amino acid sequence residues from the C-telopeptide region of the α1(I) chain of Type I collagen, sometimes at least eight or nine, and sometimes as many as eighteen residues derived from a selected C-telopeptide sequence (Seq. ID No. 1) as set forth herein. The term "peptide" is used in the present specification to designate a series of amino acids connected one to the other by peptide bonds between the alpha-amino and carboxy groups of adjacent amino acids.

The peptides can be prepared via chemical synthesis, as described hereinbelow, or by recombinant DNA technology. The peptide will preferably be substantially free of naturally occurring Type I collagen proteins and fragments thereof, other than the C-telopeptide. The peptides can be either in their neutral (uncharged) forms or in forms which are salts, and either free of modifications, such as glycosylation, side chain oxidation, or phosphorylation, or containing these modifications, subject to the condition that the modification not destroy the immunoreactivity of the peptide as herein described.

Desirably, the peptide will be as small as possible, while still maintaining substantially all of the immunoreactivity of a larger peptide. By "immunoreactivity," it is meant the ability of a peptide of the present invention to immunologically compete with the C-telopeptide of the α1(I) chain of Type I collagen, and/or which has the ability, when used as an immunogen, to stimulate the production of antibodies, which are capable of specifically binding to the C-telopeptide of the α1(I) chain of Type I collagen.

A preferred immunoreactive C-telopeptide of the present invention is derived from the C-terminus region, amino acid residues 1036 to 1053 of the α1(I) chain of human type I collagen. A representative peptide embodiment of this region is the peptide of the following sequence:

(SEQ ID NO:1)
Asp—Phe—Ser—Phe—Leu—Pro—Gln—Pro—Pro—
Gln—Glu—Lys—Ala—His—Asp—Gly—Gly—Arg wherein the peptide can be optionally flanked and/or modified at one or both of the N- and C-termini, as desired, by additional amino acids from the α1(I) Type I carboxy terminal region, additional amino acids to facilitate linking, labeling, other N- and C-terminal modifications, and linkage to carriers, etc., as further described herein. In a particularly preferred embodiment of SEQ ID NO:1, the N-terminal further includes Tyr-Cys residues for convenient labeling, polymerization via disulfide bonds, adsorption, etc., as desired for a particular application. Thus, one peptide modified from SEQ ID NO:1 has the sequence:

[SEQ ID NO:2]
Cys—Tyr—Asp—Phe—Ser—Phe—Leu—Pro—Gln—Pro—
Pro—Gln—Glu—Lys—Ala—His—Asp—Gly—Gly—Arg and is described in further detail in the Examples below.

As mentioned above, additional amino acids can be added to the termini of a peptide to provide for ease of linking peptides one to another, for coupling to a carrier, support or larger peptide, and for modifying the physical or chemical properties of the peptide, etc. One or more amino acids, such as tyrosine, cysteine, lysine, glutamic or aspartic acid, or the like, can be introduced at the C- or N-terminus of the peptide. In addition, a peptide sequence can differ from the native human C-telopeptide sequence of α1(I) chain of Type I by being modified by amino terminal acylation, e.g., acetylation, or thioglycolic acid amidation, carboxy terminal amidation, e.g., ammonia, methylamine, etc. In some instances these modifications may provide sites for linking to a support or other molecule.

It will be understood that the peptides of the present invention or analogs thereof, which have immunoreactivity with the C-telopeptide of the α1(I) chain Type I collagen, may be modified as necessary to provide other desired attributes, e.g., improved immunoreactivity (such as increased immunocompetition with native protein), improved adsorption to a solid phase, etc., while increasing or at least not significantly diminishing the immunoreactivity of the unmodified peptide, which is derived from the native procollagen sequence. For instance, the peptides may be subject to various changes, such as insertions, deletions, and substitutions, either conservative or non-conservative, where such changes might provide for certain advantages in their use. By conservative substitutions is meant replacing an amino acid residue with another, which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Usually, the portion of the sequence which is intended to substantially mimic an immunoreactive procollagen epitope will not differ by more than about 20% from the native procollagen sequence, except where additional amino acids may be added at either terminus for the purpose of modifying the physical or chemical properties of the peptide for, e.g., ease of linking or coupling, and the like.

Having identified different peptides of the invention, which are immunoreactive with the C-telopeptide, in some instances it may be desirable to join two or more peptides in a composition or admixture. The peptides in the composition can be identical or different and together, they should provide equivalent or greater immunoreactivity than the parent peptide(s). For example, using the methods described herein, two or more peptides may define different or overlapping immunoreactive epitopes from the same or different C-telopeptide subsequences, which peptides can be combined in a cocktail to provide enhanced immunoreactivity.

The peptides of the invention can be combined via linkage to form polymers. Where the same peptide is linked to itself, thereby forming a homopolymer, a plurality of repeating epitopic units are presented. When the peptides differ, e.g., a cocktail representing different procollagen regions, heteropolymers with repeating units are provided. In addition to covalent linkages, noncovalent linkages capable of forming intermolecular and intrastructural bonds are also contemplated by the present invention.

Linkages for homo- or hetero-polymers or for coupling to carriers can be provided in a variety of ways. For example, cysteine residues can be added at both the amino and carboxy-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, *Immun. Rev.* 62:185 (1982), which is incorporated herein by reference. Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl 4-(N-maleimidomethyl) cyclohexane-1-carboxylate (SMCC). Of course, it will be understood that linkage should not substantially interfere with the immunoreactivity of either of the linked groups.

As mentioned above, amino acid arms may be provided at the C- and/or N-terminus of the peptide or oligopeptide. If present, the arms will usually be at least one amino acid and may be 50 or more amino acids, more often 1 to 10 amino acids, and preferably less than 5 amino acids for ease of synthesis. The arms may serve a variety of purposes, such as spacers, to attach peptides to a carrier, or to immobilize peptides to a solid phase, etc. To provide useful functionalities for linking to a carrier, or solid phase or to form higher-ordered structures, such as dimers, trimers, or other multimers, amino acids, such as tyrosine, cysteine, aspartic acid, or the like, may be provided at the C- and/or N-terminus of the arm or peptide. To enhance epitope presentation and/or radiolabeling, of particular interest is the presence of from 1 to 10 amino acids at the C- and/or N-terminus, more preferably 1 to 5 amino acids, and most preferably about 1 to 3. Particularly preferred embodiments of certain peptides described herein are obtained when 2 amino acids are added as an arm, generally at the N-terminus, with the N-terminal residue of the arm preferably Cys. In exemplary embodiments the spacer residues between the peptide and the terminal functional group are Gly. A terminal Cys residue may also be linked through a disulfide linkage to a dithio- or thio-functionalized support or a thioether linkage to an activated olefin support.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984); Tam et al., *J. Am. Chem. Soc.* 105:6442 (1983); Merrifield, *Science* 232:341–347 (1986); and Barany and Merrifield, *The Peptides*, Gross and Meienhofer, eds., Academic Press, New York, pp. 1–284 (1979), each of which is incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify immunoreactive peptides having immunodominant epitopes of the C-telopeptide of the α1(I) chain of Type I collagen.

Alternatively, recombinant DNA technology may be employed, wherein a nucleotide sequence which encodes an α1(I) Type I carboxy terminal peptide of the invention is inserted into an expression vector, transformed or transfected into an appropriate host cell and cultivated under conditions suitable for expression. These procedures are generally known in the art, as described generally in Sambrook et al., *Molecular Cloning. A Laboratory Manual*, Cold Spring Harbor Press, Cold Spring Harbor, N.Y. (1989); Ausubel et al., (ed.) *Current Protocols in Molecular Biology*, John Wiley and Sons, Inc., New York (1987), and U.S. Pat. Nos. 4,237,224, 4,273,875, 4,431,739, 4,363,877 and 4,428,941, for example, whose disclosures are incorporated herein by reference. Thus, fusion proteins, which comprise one or more peptide sequences of the invention, can be used to present the determinants of the C-telopeptide of the α1(I) chain of Type I collagen.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors can be used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

The peptides and antibodies of the present invention and compositions thereof find particular use as diagnostic reagents. For example, a peptide as described herein, and/or antibodies to the peptide, may be used to determine the rate of bone resorption in an individual. Diagnostic assays for bone resorption, often in conjunction with bone formation assays, can be used to assess net bone balance in an individual. An increase in bone resorption without an adequate compensatory increase in bone formation may result in osteoporosis or other bone disorder. The amount of free C-telopeptide in a particular individual can be monitored over a period of time and progression or regression of bone resorption can be determined. Samples from an individual can also be compared to relative levels determined from a group of similar patients and the variation therefrom used as a marker of disease progression or regression. Thus, the diagnostic assays provided herein can also be used to assess the responsiveness of an individual to a particular treatment regimen for a bone resorption-related disorder, to modify a treatment protocol, or to establish a prognosis for an affected individual. In addition, the diagnostic assays can be used to predict which individuals will be at substantial risk for developing bone-resorption disorders, such as, e.g., osteoporosis.

Purified polyclonal or monoclonal antibodies, which bind to the peptides of the invention also find use in immunocytochemistry, such as immunoaffinity purification of the α1(I) chain of Type I collagen, where immunopurification techniques are generally known in the art and can be adapted using the anti-peptide antibodies described herein to isolate the α1(I) chain of Type I collagen in substantially pure form, as desired. Patient samples can also be analyzed for the presence of C-telopeptide, using the antibodies prepared against the peptides in Western blot techniques, which are described in U.S. Pat. No. 4,452,901, incorporated herein by reference. The antibodies and peptides of the invention can find use in a wide variety of other assays, e.g., screening of genetic libraries, and the like.

As will be recognized by those skilled in the art, numerous types of immunoassays are available for use in the present invention. For instance, direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, New York (1988), each of which is incorporated by reference herein.

The samples to be assayed may be derived from extracellular fluid, cell components or cell products, including, but not limited to, cells and cell culture supernatants, cell extracts, tissue extracts, wound fluids, urine, blood, plasma, serum, and fractions thereof, but urine is particularly preferred. As the C-telopeptide is believed to be extracellularly cleaved from the α1(I) chains of Type I collagen, typically the biological sample will be an extracellular fluid or derived therefrom.

The peptide and antibody compositions may be used unlabeled or labeled depending upon their application. By "label" is intended a molecule which provides, directly or indirectly, a detectable signal. Various labels may be employed, such as radionuclides (e.g., $^{125}$I, $^{131}$I, $^{3}$H, $^{14}$C), enzymes, fluorescers, chemiluminescers, enzyme substrates, cofactors or inhibitors, particles (e.g., magnetic particles), combinations of ligands and receptors (e.g., avidin and biotin), dyes, or the like. In addition, the peptides and antibodies thereto may be modified in a variety of ways for binding to a particular surface, such as a microtiter plate, glass or latex bead, tube, filter, chromatographic surface, nitrocellulose paper, cellulose, silica gel, or the like. The particular manner in which peptides and antibodies may be joined to another compound or solid phase surface finds ample illustration in the literature. See, for example, U.S. Pat. Nos. 4,371,515; 4,487,715; and patents cited therein. As mentioned above, reagents such as p-maleimidobenzoic acid, p-methyldithiobenzoic acid, maleic acid anhydride, succinic acid anhydride, glutaraldehyde, hetero-bifunctional cross-linkers, and the like are commonly used for such purposes.

In one assay format, the amount of C-telopeptide in a biological sample is determined in a competition-type assay by measuring the extent that C-telopeptide in the sample competes with a peptide of the present invention for binding to antibodies specific for the peptide. Although several competitive assay formats are known, in one fluid phase competition assay, such as radioimmunoassay, antibodies and peptides (labeled or capable of being labeled) are allowed to interact in a buffered system under conditions conducive to immune complex formation. A sample suspected of containing the C-telopeptide is then added and the system generally allowed to reach equilibrium. An optional wash step to separate bound reactants from unbound may be used to enhance sensitivity or specificity. The immune complexes resulting from the incubation are subsequently detected, the amount of label determined being proportional to the amount of labeled peptides of the invention bound to the antibody. Alternatively, the sample can first be incubated with the antibody and, subsequently or simultaneously, incubated with a labeled peptide of the invention.

In a solid phase competition type immunoassay the primary antibody, which is immunologically reactive with an epitope contained within the sequence of one of the peptides of the invention, such as, e.g., SEQ ID NO:1, where the epitope is immunologically competitive with an epitope of the C-telopeptide, is bound, covalently or noncovalently, to a carrier, typically an insoluble solid phase, such as a microtiter well. The biological sample to be tested is incubated with the antibody under conditions conducive to immune complex formation, and either simultaneously or subsequently contacted with at least one of the labeled peptides of the invention, also under conditions conducive to immune complex formation. Specifically bound label is then detected, and the presence or quantity of C-telopeptide in the sample determined. Typically, the amount of labeled peptide, which is bound to the antibodies, is proportional (inversely) to the amount of C-telopeptide in the sample. Separation steps (e.g., either physicochemical or immunological) and wash steps may be necessary to distinguish specific binding over background.

In an ELISA type immunoassay, again a variety of formats are contemplated. In one method, a peptide of the invention is bound to a solid phase, e.g. microtiter well, by adsorption, cross-linking, etc. A test sample, such as urine or plasma, is incubated with the anti-peptide antibodies of the invention, and the mixture is placed in the peptide-coated well and incubated. Antibody, which is not bound by C-telopeptide in the sample, is bound to the peptide on the solid phase. After a separation step, the presence and quantity of bound antibodies can be determined, e.g., using a labeled secondary antibody, such as anti-rabbit IgG/IgM when the primary antibodies are produced as rabbit antisera, or a labeled protein specific for immune complexes, such as *S. aureus* protein A or protein G, and a convenient color substrate as necessary.

Kits can also be supplied for use with the recombinant or synthetic C-telopeptides or antibodies of the present invention in determining levels of bone resorption in an individual. Thus, the subject peptide compositions may be provided, usually in lyophilized form, in a container, either alone or in conjunction with additional reagents, such as the C-telopeptide-specific antibodies, labels, and/or anti-antibodies, and the like. The peptides and antibodies, which may be conjugated to a label or unconjugated, are included in the kits with buffers, such as Tris, phosphate, carbonate, etc., stabilizers, biocides, inert proteins, e.g., serum albumin, or the like. Frequently, it will be desirable to include an inert extender or excipient to dilute the active ingredients, where the excipient may be present in from about 1 to 99% of the total composition. Where antibodies capable of binding to the C-telopeptide and to the peptides of the invention are employed in an assay, they will typically be present in a separate vial.

Monoclonal antibodies for diagnostic uses, which bind the C-telopeptide and peptides of the present invention, can be produced by a variety of means. The production of murine monoclonal antibodies is well known and may be accomplished by, for example, immunizing the animal with a recombinant or synthetic peptide molecule or a selected portion thereof (e.g., an epitopic domain which competes with an epitope of the C-telopeptide). Antibody producing cells obtained from the immunized animal are immortalized and screened, or screened first for, e.g., the production of antibody, which functions in a competition assay using peptides and C-telopeptide in a sample, and then immortalized. Antisera (polyclonal antibodies) or monospecific antibodies typically are non-human in origin, such as rabbit, goat, or mouse, etc., and can be prepared by immunizing with appropriate peptides, which often will be conjugated to a carrier, e.g., keyhole limpet hemocyanin or bovine serum albumin, for increased immunogenicity. The preparation of antibodies in this manner is well known in the art, such as described in Harlow and Lane, supra.

The following examples are offered by way of illustration, not by way of limitation.

EXAMPLE I

Measurement of C-telopeptide in Children and Adults

This example illustrates preparation and use of antibodies for the detection of C-telopeptide in human serum. The assays demonstrated the C-telopeptide levels are higher in children than adults.

Antibodies to the C-telopeptide source were produced. New Zealand White rabbits and Hartley guinea pigs were immunized by monthly intradermal injections of 50 μg of the purified C-telopeptide emulsified in Titer-Max adjuvant CytRx Corporation, Norcross, Ga. 30092. Serum samples were withdrawn at regular intervals to test for antibody titer. Although all animals developed antibodies to the peptide, the titers of the individual animals varied. One rabbit and one guinea pig, which developed the highest antibody titers, were used for all subsequent characterizations.

The polyclonal antibodies obtained as above were used in radioimmunoassays (RIA) to determine C-telopeptide levels in normal adults and children. The diluent for all RIA procedures was 0.05 mol/L sodium borate, pH 8.4, supplemented with 0.1% BSA and 0.05% sodium azide. The final antisera dilution used during the assays was 1:5000, a dilution sufficient to bind 25% of the added tracer. After overnight incubation at 4° C., phase separation was accomplished by the addition of 100 μl of a 1:20 dilution of nonimmune serum, 400 μl of a 1:20 dilution of goat anti-IgG, and 200 μl polyethylene glycol 8000, 8% wt/vol in distilled water. The samples were thoroughly mixed and incubated for three hours at room temperature. The precipitates were pelleted by centrifugation and the supernatant decanted. Values were determined using the log-logit method of Rodbard et al., "Data Processing for Radioimmunoassays: An Overview" in *Clinical Chemistry and Immunochemistry Chemical Bases and Applications in Disease*, Natelson, Pesce and Dietz, eds., American Association of Clinical Chemists, Washington, D.C., 1978, pp. 477–494.

Human urine and sera from 11 normal adults and 15 normal children were collected at random times during the day. The ages of the adults ranged from 23 to 46 years, while that of the children ranged from 9 to 15 years. Sera were aliquotted and stored frozen at −70° C. until assayed. Each aliquot was assayed one time and then discarded. Urine was collected from normal adults and children and stored frozen at −20° C. until used. Serum samples were assayed with rabbit antiserum and urine samples were assayed with guinea pig antiserum.

The mean values of C-telopeptide found in the sera of normal adults and children are shown in FIG. 1. The amount found in adults was 1.03±0.41 ng/mL, while that found in children was 8.00±3.37. The urinary C-telopeptide to creatinine ratio was also 67% higher in children than in adults. The significant increases in the serum and urine levels of the peptide in children reflect the greater rate of bone remodelling in growing children. Furthermore, the great discriminate power of the assay to distinguish between these two metabolic conditions is indicated by Z-score analysis (Serum Z-score=14.6; Urine Z-score=5.1). The Z-score was calculated as described in "Basic Medical Statistics," Anita K. Bahn, Grune & Stratton, N.E. 1972.

EXAMPLE 2

Measurement of C-telopeptide in Osteoporosis

Urinary C-telopeptide levels were determined from patients having clinical osteoporosis and normal patients. The C-telopeptide levels were determined as in Example 1 using guinea pig antiserum. The urinary C-telopeptide to creatinine ratio was determined and found to be significantly higher in osteoporotic patients than in normal patients (3.45 vs. 2.35; Z-score -3.65). The results are provided in Table 1 below.

TABLE 1

| OSTEOPOROTICS - vs - CONTROLS | | | |
|---|---|---|---|
| Subject Normal | C-Telo ng/mL | CRT mg/mL | C-Telo/CRT ng/m |
| VMP | 4.31 | 2.17 | 1.99 |
| NIC | 3.05 | 1.36 | 2.24 |
| DI | 4.51 | 1.74 | 2.59 |
| AKT | 3.89 | 1.51 | 2.58 |
| Osteoporotic | | | |
| MC | 1.80 | 0.53 | 3.40 |
| VM | 3.36 | 1.26 | 2.67 |
| DM | 2.67 | 0.64 | 4.17 |
| IT | 3.38 | 1.08 | 3.13 |
| MM | 2.93 | 0.65 | 4.51 |
| GF | 2.93 | 1.03 | 2.84 |
| MEAN NORMAL | | 2.35 | |
| STD | | 0.25 | |
| MEAN OP | | 3.45 | |
| STD | | 0.67 | |
| Z-SCORE NORMAL -vs- OP | | −3.65 | |

Although the foregoing invention has been described in some detail by way of illustration and example for purposes of clarity of understanding, it will be apparent that certain changes and modifications may be practiced within the scope of the appended claims.

What is claimed is:

1. A method for determining the presence of a C-telopeptide of type I collagen in an individual, comprising:

(a) incubating, under conditions conducive to the formation of immune complexes,
  (i) a sample from said individual, suspected of containing C-telopeptide of type I collagen, and
  (ii) a C-telopeptide antibody, which binds to a first epitope of said C-telopeptide of type I collagen and which also binds to a second epitope which is immunologically competitive with the first epitope, wherein said second epitope is contained within the sequence Asp-Phe-Ser-Phe-Leu-Pro-Gln-Pro-Pro-Gln-Glu-Lys-Ala-His-Asp-Gly-Gly-Arg (SEQ ID NO: 1), and said sequence lacks hydroxylysyl pyridinoline crosslinks or lysyl pyridinoline crosslinks; and (b) determining the extent of formation of said immune complexes of said C-telopeptide of type I collagen and said C-telopeptide antibody, wherein the extent of formation of said immune complexes correlates to the presence of the C-telopeptide of type I collagen in said individual.

2. The method of claim 1, wherein said sample is human serum, plasma, urine, wound fluid, or cell culture supernatant.

3. The method of claim 2, wherein the sample is human urine.

4. The method of claim 1, wherein said C-telopeptide antibody is a polyclonal or monoclonal antibody made by a process comprising immunizing an animal with a recombinant or synthetic peptide having from six to fifty amino acids, wherein said peptide has said second epitope contained within the sequence Asp-Phe-Ser-Phe-Leu-Pro-Gln-Pro-Pro-Gln-Glu-Lys-Ala-His-Asp-Gly-Gly-Arg (SEQ ID NO: 1) and said peptide lacks hydroxylysyl pyridinoline crosslinks or lysyl pyridinoline crosslinks.

5. The method of claim 1, further comprising incubating, under conditions conducive to the formation of immune complexes, a second antibody with said sample prior to, simultaneously with, or subsequent to the incubation of said sample and said C-telopeptide antibody, wherein said second antibody binds to said immune complexes.

6. The method of claim 5, wherein one of said C-telopeptide antibody or said second antibody is immobilized on a support while the other of said C-telopeptide antibody or said second antibody is labeled to provide a detectable signal, and the extent of formation of said immune complexes is determined by detecting the signal either bound to said support or remaining in solution.

7. The method of claim 6, wherein said C-telopeptide antibody or said second antibody is labeled with an enzyme, a fluorescer, a radionuclide, a chemiluminescer, or a dye.

8. The method of claim 1, further comprising incubating, under conditions conducive to the formation of immune complexes, a peptide with said C-telopeptide antibody prior to, simultaneously with, or subsequent to, the incubation of said sample and said C-telopeptide antibody, wherein said peptide contains said second epitope and said peptide competes with said C-telopeptide of type I collagen for binding to said C-telopeptide antibody.

9. The method of claim 8, wherein said peptide has the sequence (SEQ ID NO:3)
Xaa—Asp—Phe—Ser—Phe—Leu—Pro—Gln—Pro—Pro—Gln—Glu—Lys—Ala—His—Asp—Gly—Gly—Arg—Xaa wherein each Xaa is optionally present and when present, is Cys or Tyr.

10. The method of claim 8, wherein one of said C-telopeptide antibody or said peptide is immobilized on a support while the other of said C-telopeptide antibody or said peptide is labeled to provide a detectable signal, and the extent of formation of said immune complexes is determined by detecting the signal either bound to said support or remaining in solution.

11. The method of claim 10, wherein said C-telopeptide antibody or said peptide is labeled with an enzyme, a fluorescer, a radionuclide, a chemiluminescer, or a dye.

12. A method for determining the presence of a C-telopeptide of type I collagen in an individual, comprising:

(a) incubating, under conditions conducive to the formation of immune complexes,
(i) a sample from said individual, suspected of containing C-telopeptide of type I collagen, and
(ii) a C-telopeptide antibody, which immunologically binds to a first epitope of said C-telopeptide of type I collagen and which also immunologically binds to a second epitope which is immunologically competitive with the first epitope, to form immune complexes between said C-telopeptide in said sample and said C-telopeptide antibody;

(b) incubating, either simultaneously with or subsequent to the incubation of said sample and said antibody, a peptide immobilized on a support, wherein said peptide contains the second epitope, said second epitope is contained within the sequence Asp-Phe-Ser-Phe-Leu-Pro-Gln-Pro-Pro-Gln-Glu-Lys-Ala-His-Asp-Gly-Gly-Arg(SEQ ID NO: 1), and said sequence lacks hydroxylysyl pyridinoline crosslinks or lysyl pyridinoline crosslinks;

(c) separating immune complexes, which are bound to the support, from unbound substances;

(d) incubating the separated immune complexes bound to the support with a second antibody which binds to said C-telopeptide antibody and is labeled to provide a detectable signal, (e) detecting the signal either bound to said support or remaining in solution; and (f) determining therefrom the presence of said C-telopeptide of type I collagen in said individual.

13. The method of claim 12, wherein said peptide has the sequence (SEQ ID NO:3)
Xaa—Asp—Phe—Ser—Phe—Leu—Pro—Gln—Pro—Pro—Gln—Glu—Lys—Ala—His—Asp—Gly—Gly—Arg—Xaa wherein each Xaa is optionally present and when present, is Cys or Tyr.

14. The method of claim 12, wherein said second antibody is labeled with an enzyme, a fluorescer, a radionuclide, a chemiluminescer, or a dye.

15. A method for monitoring the rate of bone degradation in an individual, comprising:

(a) incubating, under conditions conducive to the formation of immune complexes,
(i) a sample from said individual, suspected of containing C-telopeptide of type I collagen, and
(ii) a C-telopeptide antibody, which binds to a first epitope of said C-telopeptide of type I collagen and which also binds to a second epitope which is immunologically competitive with the first epitope, wherein said second epitope is contained within the sequence Asp-Phe-Ser-Phe-Leu-Pro-Gln-Pro-Pro-Gln-Glu-Lys-Ala-His-Asp-Gly-Gly-Arg (SEQ ID NO: 1), and said sequence lacks hydroxylysyl pyridinoline crosslinks or lysyl pyridinoline crosslinks; and (b) determining the extent of formation of said immune complexes of said C-telopeptide of type I collagen and said C-telopeptide antibody, in samples taken over a period of time from said individual, wherein the extent of formation of said immune complexes correlates to the presence of the C-telopeptide of type I collagen in said individual and an increase in the relative concentration of said C-telopeptide of type I collagen is indicative of bone degradation.

16. The method of claim 15, further comprising incubating, under conditions conducive to the formation of immune complexes, a second antibody with said sample prior to, simultaneously with, or subsequent to the incubation of said sample and said C-telopeptide antibody, wherein said second antibody binds to said immune complexes.

17. The method of claim 15, further comprising incubating, under conditions conducive to the formation of immune complexes, a peptide with said C-telopeptide antibody prior to, simultaneously with, or subsequent to, the incubation of said sample and said C-telopeptide antibody, wherein said peptide contains said second epitope and said peptide competes with said C-telopeptide of type I collagen for binding to said C-telopeptide antibody.

18. The method of claim 17, wherein said peptide has the sequence (SEQ ID NO:3)

Xaa—Asp—Phe—Ser—Phe—Leu—Pro—Gln—Pro—Pro—Gln—Glu—Lys—Ala—His—Asp—Gly—Gly—Arg—Xaa wherein each Xaa is optionally present and when present, is Cys or Tyr.

19. A test kit for determining the presence of a C-telopeptide of type I collagen in an individual, wherein said kit comprises:
   an antibody, which immunologically binds to a first epitope of said C-telopeptide of type I collagen and which also immunologically binds to a second epitope which is immunologically competitive with the first epitope; and
   a peptide which is labeled to provide a detectable signal, contains from six to fifty amino acids, and includes the second epitope, wherein said second epitope is contained within SEQ ID NO: 1, and said sequence lacks hydroxylysyl pyridinoline crosslinks or lysyl pyridinoline crosslinks.

20. The test kit of claim 19, wherein said peptide has the sequence (SEQ ID NO:3)

Xaa—Asp—Phe—Ser—Phe—Leu—Pro—Gln—Pro—Pro—Gln—Glu—Lys—Ala—His—Asp—Gly—Gly—Arg—Xaa wherein each Xaa is optionally present and when present, is Cys or Tyr.

21. The test kit of claim 19, wherein said antibody is a polyclonal or monoclonal antibody made by a process comprising immunizing an animal with a recombinant or synthetic peptide having from six to fifty amino acids, wherein said peptide has said second epitope contained within the sequence Asp-Phe-Ser-Phe-Leu-Pro-Gln-Pro-Pro-Gln-Glu-Lys-Ala-His-Asp-Gly-Gly-Arg (SEQ ID NO: 1) and said peptide lacks hydroxylysyl pyridinoline crosslinks or lysyl pyridinoline crosslinks.

22. A monoclonal antibody which binds to an epitope of a C-telopeptide of type I collagen and which also binds to a second epitope, wherein said second epitope is contained within the sequence Asp-Phe-Ser-Phe-Leu-Pro-Gln-Pro-Pro-Gln-Glu-Lys-Ala-His-Asp-Gly-Gly-Arg (SEQ ID NO: 1) and said sequence lacks hydroxylysyl pyridinoline crosslinks or lysyl pyridinoline crosslinks.

23. The monoclonal antibody of claim 22, wherein said monoclonal antibody is made by a process comprising immunizing an animal with a recombinant or synthetic peptide having from six to fifty amino acids, wherein said peptide has said second epitope contained within the sequence Asp-Phe-Ser-Phe-Leu-Pro-Gln-Pro-Pro-Gln-Glu-Lys-Ala-His-Asp-Gly-Gly-Arg (SEQ ID NO: 1) and said peptide lacks hydroxylysyl pyridinoline crosslinks or lysyl pyridinoline crosslinks.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

```
Asp Phe Ser Phe Leu Pro Gln Pro Pro Gln Glu Lys Ala His Asp Gly
  1           5                   10                  15
Gly Arg
```

( 2 ) INFORMATION FOR SEQ ID NO:2:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

```
Cys Tyr Asp Phe Ser Phe Leu Pro Gln Pro Pro Gln Glu Lys Ala His
  1           5                   10                  15
Asp Gly Gly Arg
              20
```

( 2 ) INFORMATION FOR SEQ ID NO:3:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

```
Xaa Asp Phe Ser Phe Leu Pro Gln Pro Pro Gln Glu Lys Ala His Asp
  1           5                   10                  15
Gly Gly Arg Xaa
              20
```